United States Patent
Scarano

(10) Patent No.: US 8,323,469 B2
(45) Date of Patent: Dec. 4, 2012

(54) SENSOR AND APPARATUS FOR ANALYSING GASES PRESENT IN BLOOD

(75) Inventor: Elio Scarano, Rome (IT)

(73) Assignee: BioTech Research and Finance Ltd., Newark, DE (US)

(*) Notice: Subject to any disclaimer, the term of this patent is extended or adjusted under 35 U.S.C. 154(b) by 707 days.

(21) Appl. No.: 12/597,981

(22) PCT Filed: Jan. 25, 2008

(86) PCT No.: PCT/IB2008/000165
§ 371 (c)(1), (2), (4) Date: Oct. 28, 2009

(87) PCT Pub. No.: WO2008/090456
PCT Pub. Date: Jul. 31, 2008

(65) Prior Publication Data
US 2010/0133100 A1  Jun. 3, 2010

(30) Foreign Application Priority Data
Jan. 25, 2007  (IT) .............................. MI2007A0110

(51) Int. Cl.
*G01N 27/413* (2006.01)
(52) U.S. Cl. .................... 204/431; 204/406; 205/780.5; 205/792
(58) Field of Classification Search ............ 204/403.01, 204/406, 431, 432; 205/780.5, 792
See application file for complete search history.

(56) References Cited

U.S. PATENT DOCUMENTS

| | | | |
|---|---|---|---|
| 3,886,058 A | 5/1975 | Barna | |
| 4,329,214 A | 5/1982 | Spritzer et al. | |
| 4,840,179 A | 6/1989 | Ullrich | |
| 5,007,424 A | 4/1991 | Ahsbahs et al. | |

FOREIGN PATENT DOCUMENTS

| | | |
|---|---|---|
| EP | 0 267 978 | 5/1988 |
| EP | 0 302 127 | 2/1989 |

OTHER PUBLICATIONS

International Search Report dated Jun. 9, 2008, from corresponding PCT application.

*Primary Examiner* — Kaj K Olsen
(74) *Attorney, Agent, or Firm* — Young & Thompson

(57) ABSTRACT

A galvanic sensor for analyzing gases present in blood includes a duct suitable for being crossed by a flow of gas and provided with an inlet opening and an outlet opening, a reference galvanic element including a container containing an electrolytic solution in which a reference electrode is inserted, and a measuring galvanic element. The container is fixed to the duct and the measuring galvanic element includes a measuring electrode arranged transversally to the axis of the duct and a filiform element having a high capillarity so as to act as a wick. The filiform element is anchored to the container and has a first end contacting the measuring electrode and a second end contacting the electrolytic solution. The measuring element of the galvanic sensor is extremely miniaturized and allows to detect in real time and continuously gases in traces, on the order of parts per million or even lower.

20 Claims, 3 Drawing Sheets

SENSOR AND APPARATUS FOR ANALYSING GASES PRESENT IN BLOOD

CROSS REFERENCE TO RELATED APPLICATIONS

This application is a 371 National Stage Entry of application PCT/IB2008/000165 filed on Jan. 25, 2008, which claims priority to application IT MI2007/A000110 filed on Jan. 25, 2007.

FIELD OF THE INVENTION

The present invention relates to a sensor and an apparatus for analysing gases present in blood and particularly for determining gases that, like ammonia, hydrogen sulfide and nitrogen monoxide, are present in blood in minimum amounts in the order of parts per million or even lower.

BACKGROUND OF THE INVENTION

It is well known that several pathological conditions may be identified by analysing the gases present in blood. The techniques commonly used for these analyses require taking blood samples through various methods and the subsequent storing of these samples in environments that are isolated, thermostated, etc., until the time of the actual analysis. This has various drawbacks well known to those skilled in the art, as well as the impossibility of carrying out a continuous monitoring of the tension of the various gases present in blood. In order to overcome such drawbacks it has been already suggested to dispense with the taking of blood samples and to carry out the determination of the gases present in blood through another way, such as for instance through a transcutaneous way or by analysing saliva samples. These techniques, in addition to being non-invasive, also allow a continuous monitoring of blood gases and the technique for sampling the gases through transcutaneous way in particular has been employed since the beginning in the pre-natal diagnostics for determining oxygen and $CO_2$ present in blood.

Apparatuses for analysing blood gases are known, generally comprised of gas sampling probes connected through pipings to apparatuses provided with sensors for measuring the gases. Numerous sensors for analysing blood gases are known, e.g. based on measuring galvanic cells that allow to measure the concentration of one or more gases.

U.S. Pat. No. 5,007,424, e.g., describes a polarographic/amperometric sensor for measuring the oxygen partial pressure in blood by means of a Clark-type electrode arrangement. The sensor may be provided with a pH electrode for the simultaneous determination of $CO_2$ partial pressure in blood.

U.S. Pat. No. 4,840,179 discloses a thermostated device for the simultaneous and continuous measurement of oxygen and $CO_2$ present in blood, based on the principle of pH measurement in an electrolyte. The gas sampling is carried out transcutaneously. However, in order to ensure satisfactory measurements of oxygen and $CO_2$, it is necessary to heat the skin at temperatures of about 42° C. in order to enhance its permeability and consequently the flow of gas.

A problem of galvanic sensors known in the art is that they do not allow to detect the presence of traces of blood gases (such as ammonia, hydrogen sulfide and nitrogen monoxide), which may be related to several pathological conditions. In particular, the gaseous ammonia present in blood may reveal liver and kidney dysfunctions, in which the concentrations increase beyond the physiological values of 0.1-0.6 ppm.

The measurement and the monitoring of gaseous ammonia could allow a rapid and sure diagnosis of diseases like hyperammoniaemia and hypoammoniaemia, diabetes and hypertension, as well as the diagnosis of infection from *Helicobacter Pylori*. The transcutaneous determination of gaseous ammonia could also be used in haemodialysis treatments and in periodic check-ups.

In the article "Identification of ammonia in gas emanated from human skin and its correlation with that in blood" by K. Nose et al., published on Analytical Sciences, December 2005, vol. 21, page 1471 and following, there is described an experimental study through which it has been possible to detect the presence of gaseous ammonia emanated from the skin and to measure its amount. The article underlines the need for collecting the gases transcutaneously by using methods that are non-painful for the patient and in real time, thus allowing to continuously monitor the variations of gaseous ammonia in blood, as well as to make measuring apparatuses also for domestic use.

SUMMARY OF THE INVENTION

It is therefore an object of the present invention to provide a sensor and an apparatus for determining blood gases, in particular traces of gases such as ammonia, hydrogen sulfide and nitrogen monoxide, in real time and by means of an analytical technique which is non-invasive, non-manipulative and non-destructive. Said object is achieved with a sensor and an apparatus, whose main features are disclosed in claim 1 and 11, respectively, while other features are disclosed in the remaining claims.

The sensor according to the present invention is a measuring galvanic cell specifically made for detecting and measuring gases that, like ammonia, hydrogen sulfide and nitrogen monoxide and present in blood gases in minimum amounts in the order of parts per million or even lower.

An advantage of the sensor according to the present invention is that is has response and recovery times in the order of seconds, thus being able to be advantageously employed for real time and continuous measurements.

Moreover, the sensor according to the invention does not require any heating of the patient's skin in order to enhance the permeability thereof to blood gases. In fact, thanks to the miniaturization of the measuring electrode, minimum amounts of gas are enough for carrying out correct and accurate measurements. The risk of skin burns is therefore completely eliminated.

Another advantage is that the sensor is very compact and thus allows a low cost manufacturing of measuring apparatuses having a reduced size, being portable and also suitable for the domestic use.

Still another advantage of the sensor according to the present invention is that it may be used together with different types of sampling probes, suitable for both the transcutaneous sampling and the in-vitro analyses of blood or saliva samples, thus allowing the maximum flexibility of use of the measurement apparatuses in which it is inserted.

BRIEF DESCRIPTION OF THE DRAWINGS

Further advantages and features offered by the sensor and apparatus according to the present invention will become clear to those skilled in the art from the following detailed and non-limiting description of some embodiments thereof with reference to the attached drawings, wherein.

DETAILED DESCRIPTION OF THE INVENTION

Figure 1:
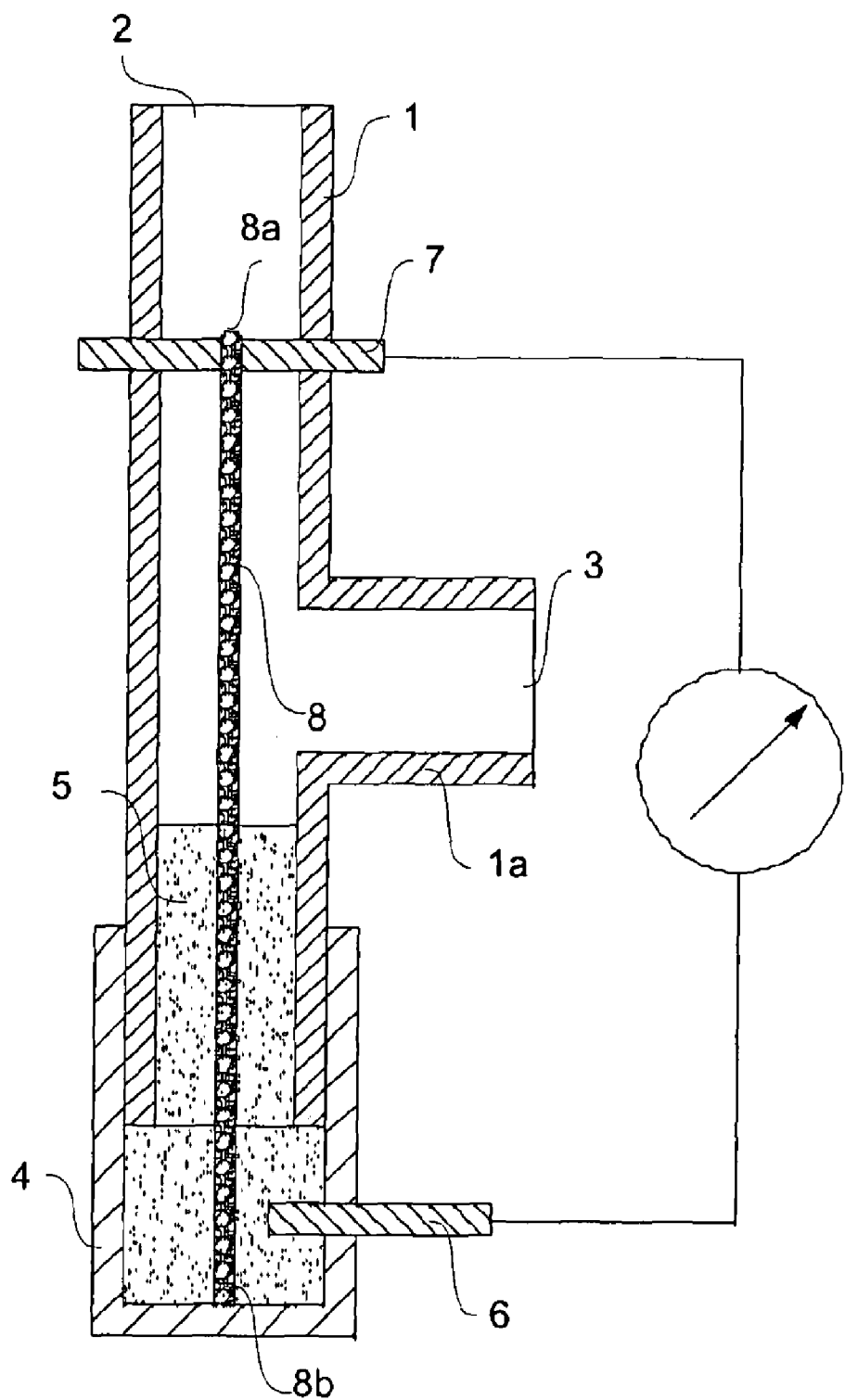
FIG. 1 shows a cross-sectional view of the sensor according to the present invention.

Referring to FIG. 1, there is seen that the galvanic sensor according to the present invention comprises a duct 1 suitable for being crossed by a flow of gas and provided with an inlet opening 2 and an outlet opening 3. Duct 1 may be made of any suitable material. For instance it may be a glass tube, which has a T shape in a preferred embodiment. Outlet 3 is arranged at a transverse arm 1a of the tube.

The sensor according to the present invention further includes a reference galvanic element, comprised of a container 4 containing an electrolytic solution 5 and of a reference electrode 6 inserted in container 4. Container 4 is fixed to duct 1, e.g. by friction or by means of a threaded connection. The measuring galvanic element of the sensor comprises a measuring electrode 7 arranged substantially transversally to the axis of duct 1 and a filiform element 8 having a high capillarity, e.g. a braided cotton yarn, anchored to container 4 and having a first end 8a contacting the measuring electrode 7 and a second end 8b contacting the electrolytic solution 5. In the embodiment shown in the drawing, the filiform element 8 is mounted in a position substantially coincident with the axis of duct 1.

The working solution wets the measuring electrode 7 by going up through the filiform element 8 by capillarity, i.e. element 8 acts as a wick. Therefore, between the measuring electrode 7 and the reference electrode 6 a potential difference based on the redox potentials of the two galvanic elements is present and can be measured.

In a preferred embodiment, the measuring electrode 7 and the reference electrode 6 are small metal bars made of stainless steel, however other materials already known for the use as electrodes may be used.

In the sensor according to the present invention, the galvanic element containing the measuring electrode is extremely miniaturized, as the volume of electrolytic solution wetting the measuring electrode 7 is determined by the very small size of the contact area between the first end 8a of the filiform element 8 and the measuring electrode 7. For example, if the electrode has a diameter of 1 mm and the filiform element has a diameter of 0.1 min, and the filiform element forms a complete coil around the electrode, the volume of electrolytic solution wetting electrode 7 is in the order of 1 μl.

On the basis of a plurality of tests carried out by the inventor with standard solutions containing a known amount of gas, it was possible to verify that such a very small volume of electrolytic solution obtained through the wicking effect of element 8 is suitable to detect amounts of gas in the order of 0.1 ppm or even lower. Similarly, by suitably choosing the diameter of the filiform element, the diameter of the electrode and the size of the contact area between the filiform element and the measuring electrode it is possible to achieve, through an adequate calibration, the desired sensibility for a correct measurement of the amounts of the desired blood gases present in blood.

This particular feature of the present invention allows to carry out analyses of the gases present in blood with minimum amounts of sampled gas and make it suitable for measuring gases that, like ammonia, hydrogen sulfide and nitrogen monoxide, are present in traces only. Therefore, in the case of a transcutaneous sampling there is no need for heating the patient's skin in order to enhance its permeability and collect a larger amount of blood gases. Moreover, the response times of the sensor are much faster since they only depend on the kinetics of the reactions occurring between the analysed gas and the electrolytic solution used in the sensor.

In the case of ammonia, for example, the electrolytic solution 5 employed may be e.g. a diluted aqueous solution of ammonium chloride.

In addition, the electrolytic solution employed must be chosen so as to avoid interferences by the other gases present in blood. In the case of a diluted aqueous solution of ammonium chloride there are no interferences from oxygen, which does not react with it. In order to avoid that $CO_2$ reacts with water, there may be advantageously exploited the fact that the reaction kinetics of $CO_2$ is much slower than that of ammonia. Thus, by suitably setting the time during which the flow of gas crosses the sensor, it is possible to completely avoid interferences by $CO_2$.

The choice of the electrolytic solution, the material and the geometry of the filiform element and the number of its coils around the measuring electrode, as well as the measuring times, are important parameters in the configuration of the sensor, which simultaneously contribute in defining its sensibility and rapidity of response.

Figure 2:
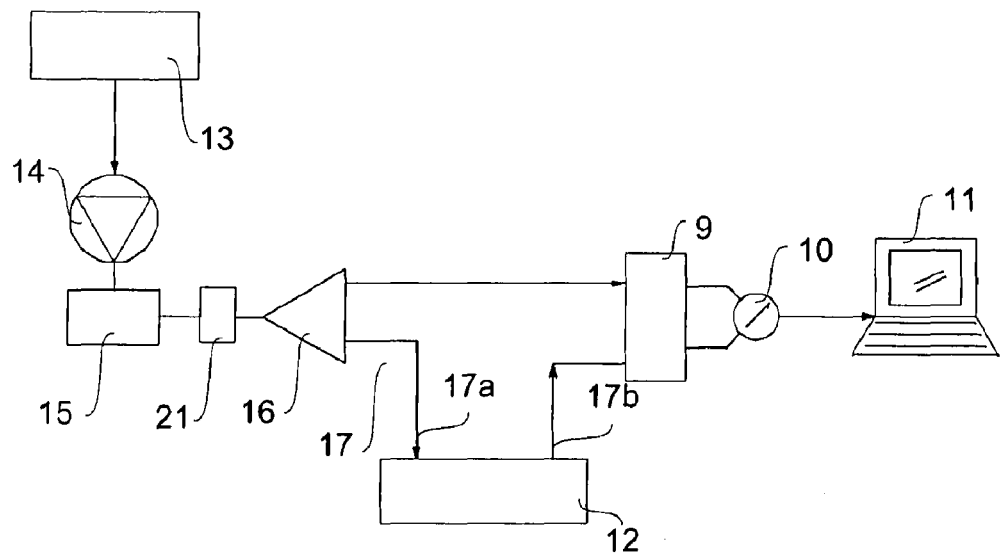
FIG. 2 shows a schematic view of a measuring apparatus including the sensor of FIG. 1.

FIG. 2 shows an apparatus for analysing blood gases, which comprises a galvanic sensor 9 according to the present invention as well as a first device 10 connected thereto and suitable for detecting a potential difference between the electrodes, e.g. a potentiometer. A second device 11, e.g. a personal computer, is connected to the first device 10 and is suitable for processing and storing potential difference data detected by the first device 10. As described above, a potential difference is present between the measuring electrode 7 and the reference electrode 6, which is based on the redox potentials of the two galvanic elements. Therefore, by measuring this potential difference over time with a potentiometer and by acquiring, storing and processing the measurements continuously, it is possible to carry out a real time monitoring of the ammonia contained in blood gases.

As shown in the drawing, the apparatus according to the present invention further comprises a probe 12 for sampling the gases. A downstream end of probe 12 is connected to the galvanic sensor 9 and an upstream end to a source 13 of a carrier gas, e.g. ambient air, which is suitable for transporting the gases present in blood towards the galvanic sensor 9. The carrier gas is pumped from source 13 by means of a pump 14 and filtered and purified through a series of filters 15 arranged downstream of pump 14. Between filters 15 and probe 12 a flow bypass 16 is arranged, allowing to direct the carrier gas alternately towards probe 12, and consequently towards the galvanic sensor 9, or directly towards the galvanic sensor 9 without crossing probe 12.

The connections among the various above-described components of the apparatus, i.e. the galvanic sensor 9, probe 12, source 13, pump 14, filters 15 and flow bypass 16, are made through tubes 17 that are impermeable to gases. These tubes 17 may be made of PTFE or stainless steel and preferably have an inner diameter of about 1 mm, suitable for ensuring a flow rate of carrier gas preferably comprised between 1 and 5 ml/s.

Figures 3, 4:
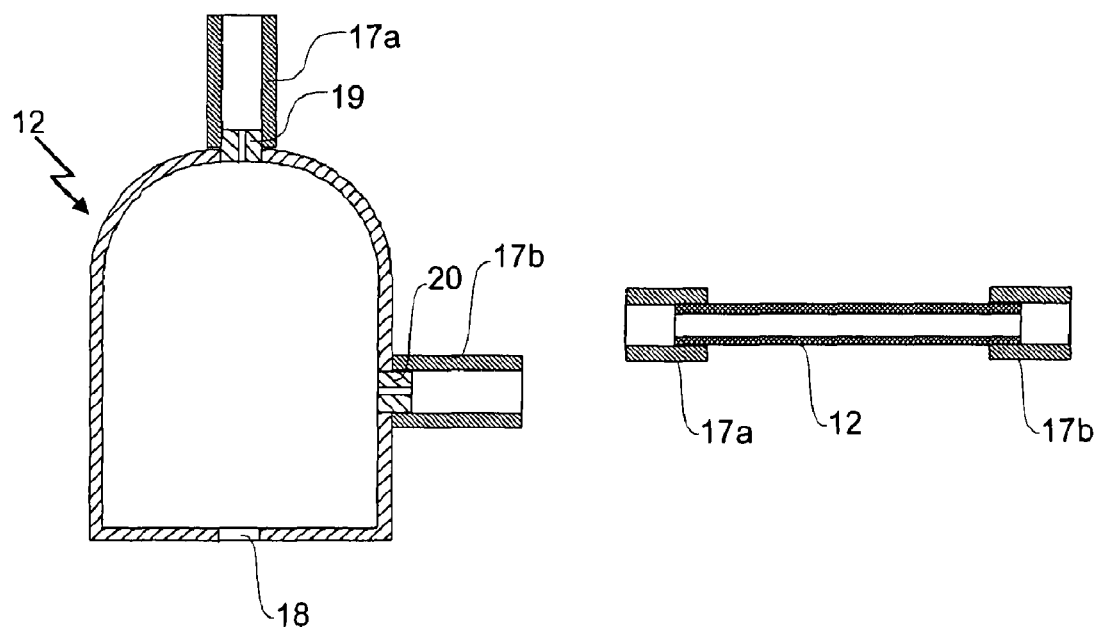
FIG. 3 shows a cross-sectional view of a first embodiment of a sampling probe that can be used with the apparatus of FIG. 2.
FIG. 4 shows a cross-sectional view of a second embodiment of a sampling probe that can be used with the apparatus of FIG. 2.

FIG. 3 shows a first embodiment of probe 12, particularly suitable for the transcutaneous sampling of the gases. The probe is comprised of a bell-shaped member having a base with an opening 18 in order to allow a transcutaneous retrieval of the gases. The bell-shaped member is also provided with an inlet 19 and an outlet 20 suitable for allowing a flow of the carrier gas through the bell. In particular, inlet 19 is connected to a tube 17a coming from the bypass 16 and outlet 20 is connected to a tube 17b leading to the galvanic sensor 9. The base opening 18 of the bell-shaped member defines an area not larger than 1 cm$^2$, which is necessary for ensuring an adequate flow of blood gases into the bell.

FIG. 4 shows a second embodiment of probe 12, which may be employed either for sampling gases through transcutaneous way or for sampling gases from blood or saliva samples collected in an analysis cell.

Probe 12 is comprised of a small tube of porous material, e.g. PTFE, having a pore diameter in the order of microns. Similarly to the bell-shaped probe, the small tube of porous PTFE is inserted between tubes 17a and 17b and is crossed by the carrier gas. In order to allow the retrieval of a sufficient amount of gas, the portion of the small tube comprised between the ends of tubes 17a and 17b has a length preferably comprised between 1 and 2 cm.

In the case of a transcutaneous sampling, the small tube is bent like a "U" and arranged astride the finger of a patient, who closes the hand thus retaining probe 12.

When sampling gases from samples of blood or saliva contained in an analysis cell, tubes 17a and 17b are airtightly inserted in a cap closing the cell, so that the small tube is suspended above the sample to be analysed.

During the operation of the apparatus, a flow of carrier gas is pumped through probe 12 for a preset measuring time $t_M$, e.g. 10 s, during which blood gases collected by probe 12 are taken and transported to the galvanic sensor 9 thus hitting the measuring electrode 7. When measuring ammonia, a portion of the molecules of ammonia enters in solution in the ammonium chloride contained inside the end of the filiform element 8 contacting the measuring electrode 7, thus forming $NH_4^+$ and $OH^-$ ions. Negative $OH^-$ ions bond to iron ions already in solution, thus altering the redox potential of the measuring element according to Nernst law. Therefore potentiometer 10, which is connected to electrodes 6 and 7, detects a potential difference that is different from the initial potential difference and may be related to the concentration of ammonia present in blood gases through a suitable calibration of the galvanic sensor 9. Subsequently, by acting on the flow bypass 16, the carrier gas is made to flow directly towards the sensor for a recovering time $t_R$, e.g. 50 s, during which the initial conditions of the galvanic sensor are restored.

A standard reference cell 21 may be optionally arranged between filters 15 and bypass 16, said cell containing a solution of the gas to be analysed at a known concentration, e.g. an aqueous solution of ammonia. In this way it is possible to set different starting conditions of the galvanic sensor 9, thus obtaining more or less rapid recovering times according to the established operation mode of the apparatus.

By repeating measuring and recovering cycles of the sensor over time, it is possible to carry out continuously the analysis of the gases present in blood, thus allowing the diagnosis of the different pathologies that may be related to blood gases as well as the monitoring of the patient.

The following examples show some cases of use of the apparatus and sensor according to the present invention.

EXAMPLE 1

An apparatus for the analysis of gases was prepared, comprising a galvanic sensor according to the present invention, a potentiometer and a computer suitable to acquire, store and process the measurements of potential difference taken by the potentiometer. The apparatus was also provided with a probe for the transcutaneous sampling of blood gases of the type shown in FIG. 4, and with a source of carrier gas, ambient air in particular, connected to a pump and a series of filters, as well as to a flow bypass, by means of a piping made of PTFE and having a diameter of 1.2 mm.

The galvanic sensor was provided with a reference element containing a diluted aqueous solution of ammonium chloride. The filiform element used was a cotton yarn having a diameter of 0.1 mm and wound so as to form one coil around a measuring electrode made of stainless steel and having a diameter of 1 mm.

The sampling probe was applied astride the middle finger of a healthy patient at the metacarpal joint, so as to be easily retained in position by closing the hand.

Three capsules containing a dose of 0.5 g of ammonium chloride each were initially administered to the patient. Subsequently the apparatus was turned on activating a flow of carrier gas at a flow rate of 3 ml/s. By acting on the bypass, the flow of carrier gas was alternately pumped through the probe for a measuring time of 10 s, thus transporting blood gases retrieved by the probe towards the sensor, and directly towards the sensor for a recovering time of 20 s.

Figure 5:
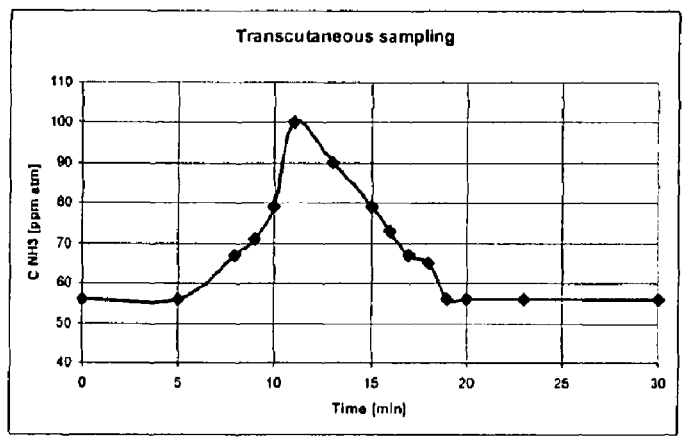
FIG. 5 is a graph showing the trend over time of gaseous ammonia concentration measured during a transcutaneous sampling with the apparatus of FIG. 2.

The apparatus was continuously operated for 30 minutes, detecting for each interval of measuring time and recovering time values of potential difference proportional to the concentration of ammonia in blood gases. These values are set forth in Table 1 below and illustrated in the graph of FIG. 5.

As it may be seen, after about 5 minutes from the administration of ammonium chloride, the values of the concentration of gaseous ammonia progressively increase up to a maximum value and then decrease to values that are equal to the initial ones.

TABLE 1

| Time [min] | ΔE [mV] | $C_{NH_3}$ [ppm atm] |
| --- | --- | --- |
| 0 | 2.7 | 56 |
| 5 | 2.7 | 56 |
| 8 | 3.2 | 67 |
| 9 | 3.4 | 71 |
| 10 | 3.8 | 79 |
| 11 | 4.8 | 100 |
| 13 | 4.3 | 90 |
| 15 | 3.8 | 79 |
| 16 | 3.5 | 73 |
| 17 | 3.2 | 67 |
| 18 | 3.1 | 65 |
| 19 | 2.7 | 56 |
| 20 | 2.7 | 56 |
| 23 | 2.7 | 56 |
| 30 | 2.7 | 56 |

EXAMPLE 2

A gas analysing apparatus similar to the apparatus described in Example 1 was prepared by airtightly inserting the probe into the cap of an analysis cell suitable for containing blood samples.

The apparatus was used during a haemodialysis cycle in the same fashion described in Example 1. During the haemodialysis cycle a patient had, as usual, a snack after about 30 minutes from the beginning of the treatment and had lunch and drank a coffee after about 60 minutes from the snack.

Samples of blood in the order of 1 g were taken at regular 30-minute intervals for a period of 4 hours by inserting a syringe in a tube transporting the patient's blood towards the inlet of the haemodialysis machine. These blood samples were treated with buffer solutions suitable for bringing the pH at a known level, e.g. 9.1.

Figure 6:
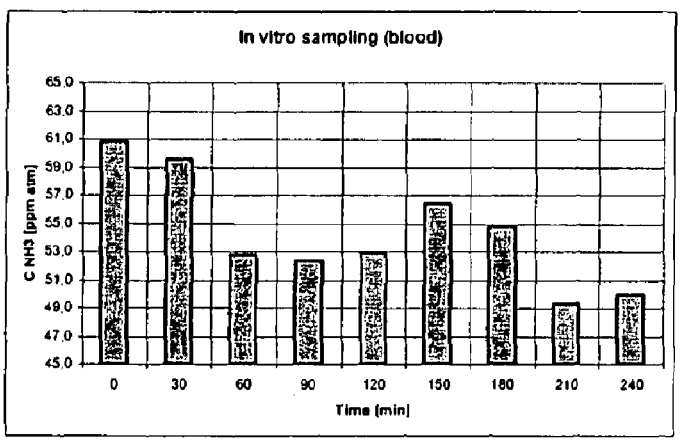
FIG. 6 is a graph showing the trend over time of gaseous ammonia concentration measured with the apparatus of FIG. 2 on blood samples taken at regular intervals during a haemodialysis cycle.

The data detected by the sensor are set forth in Table 2 below and in the graph of FIG. 6 and show how the variations in the concentration of the ammonia contained in blood gases may be related to the assumption of food by the patient and to the subsequent digestion step. In particular, the content of ammonia initially decreases as an effect of the filtering operated by the haemodialysis machine and increases after the assumption of food during the digestion step.

TABLE 2

| Time [min] | ΔE [mV] | $CNH_3$ [ppm atm] |
|---|---|---|
| 0 | −26.5 | 60.8 |
| 30 | −26.0 | 59.6 |
| 60 | −23.0 | 52.8 |
| 90 | −22.7 | 52.4 |
| 120 | −23.1 | 53.0 |
| 150 | −24.6 | 56.4 |
| 180 | −23.9 | 54.8 |
| 210 | −21.5 | 49.3 |
| 240 | −21.8 | 50.0 |

Figure 7:
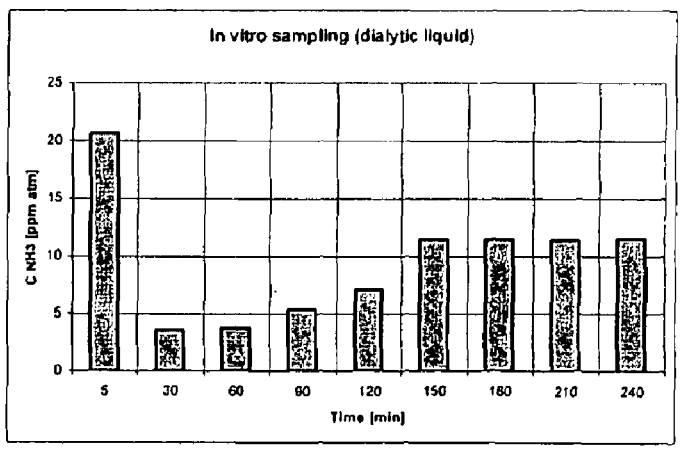
FIG. 7 is a graph showing the trend over time of gaseous ammonia concentration measured with the apparatus of FIG. 2 on samples of discharged dialytic fluid taken at regular intervals during a haemodialysis cycle.

For a comparative purpose, Example 2 was repeated on samples of discharged dialytic fluid taken during the same haemodialysis treatment, thus proving the correlation between the variations in the concentration of gaseous ammonia in blood and the variations in the concentration of ammonia in the discharged dialytic fluid. The data detected by the sensor are set forth in Table 3 below and in the graph of FIG. 7.

TABLE 3

| Time [min] | ΔE [mV] | $CNH_3$ [ppm atm] |
|---|---|---|
| 5 | −37.8 | 20.7 |
| 30 | −6.5 | 3.6 |
| 60 | −6.8 | 3.7 |
| 90 | −9.8 | 5.4 |
| 120 | −13.0 | 7.1 |
| 150 | −21.0 | 11.5 |
| 180 | −20.9 | 11.4 |
| 210 | −20.8 | 11.3 |
| 240 | −21.0 | 11.5 |

The above described and illustrated embodiments of the sensor and apparatus according to the invention are only examples susceptible of numerous variants. In particular, it is possible to make other sampling probes according to the parts of the body chosen for analysing the gases present in blood, such as, for example, compact tubular probes made of silicon rubber that may be inserted in the oral cavity of the patient between the palate and the tongue.

The invention claimed is:

1. A sensor for analysing gases comprising a duct (1) suitable for being crossed by a flow of gas and provided with an inlet opening (2) and an outlet opening (3), a galvanic reference element comprised of a container (4) containing an electrolytic solution (5) in which a reference electrode (6) is inserted, and a galvanic measuring element comprising a measuring electrode (7) and a wick (8) associated to said measuring electrode (7) and suitable for defining an electrode/electrolyte interface thereon, characterized in that said container (4) is fixed to said duct (1) and the measuring electrode (7) is arranged transversally to the axis of the duct (1), the wick (8) being in the form of a filiform element anchored to the container (4) and having a first end (8a) contacting the measuring electrode (7) and a second end (8b) contacting said electrolytic solution (5), the wick (8) forming at least one coil around the measuring electrode (7).

2. A sensor according to claim 1, characterized in that the volume of electrolytic solution (5) wetting the measuring electrode (7) is on the order of 1 μl.

3. A sensor according to claim 1, characterized in that the duct (1) is a T-shaped glass tube, the gas inlet (2) being arranged at one end of the tube and the gas outlet (3) being arranged on a transverse arm (1a) of the tube.

4. A sensor according to claim 1, characterized in that the electrolytic solution (5) is a diluted aqueous solution of ammonium chloride.

5. A sensor according to claim 1, characterized in that the measuring electrode (7) is a small metal bar.

6. A sensor according to claim 5, characterized in that the measuring electrode (7) is made of stainless steel.

7. A sensor according to claim 1, characterized in that the reference electrode (6) is a small metal bar.

8. A sensor according to claim 7, characterized in that the reference electrode (6) is made of stainless steel.

9. A sensor according to claim 1, characterized in that the wick (8) is made of cotton.

10. A sensor according to claim 9, characterized in that the wick (8) is a braided cotton yarn.

11. An apparatus for analysing blood gases, characterized by comprising a galvanic sensor (9) according to claim 1, a first device (10) connected thereto and suitable for measuring a potential difference between the measuring electrode (7) and the reference electrode (6) of the sensor (9), and a second device (11) connected to said first device (10) and suitable for acquiring, storing and processing the potential difference measurements taken by the first device (10).

12. An apparatus according to claim 11, characterized by further comprising a probe (12) for sampling blood gases, the galvanic sensor (9) being connected downstream of the probe (12) and a carrier gas source (13) being connected upstream of the probe (12), the carrier gas being pumped from said source (13) by means of a pump (14) and filtered and purified by means of a series of filters (15) arranged downstream of said pump (14), a flow bypass (16) being arranged between said filters (15) and said probe (12) and the components (9, 12, 13, 14, 15, 16) of the apparatus being connected through a piping of gas impermeable tubes (17).

13. An apparatus according to claim 12, characterized in that said probe (12) for sampling gases is comprised of a bell-shaped member having an opening (18) in the base suitable for allowing a transcutaneous retrieval of the gases.

14. An apparatus according to claim 13, characterized in that the probe (12) is also provided with an inlet (19) and an outlet (20), said inlet (19) being connected to a tube (17a) coming from the bypass (16) and said outlet being connected to a tube (17b) leading towards the galvanic sensor (9).

15. An apparatus according to claim 14, characterized in that the opening (18) in the base of the probe (12) defines an area not larger than 1 cm$^2$.

16. An apparatus according to claim 12, characterized in that said gas sampling probe (12) is comprised of a small tube made of porous material, said tube having its ends respectively inserted between a tube (17a) coming from the bypass (16) and a tube (17b) leading towards the galvanic sensor (9), and having a free portion suitable for allowing the retrieval of the gases.

17. An apparatus according to claim 16, characterized in that said porous material is PTFE and the pore diameter is in the order of microns.

18. An apparatus according to claim 16, characterized in that the free portion of the small tube of porous material comprised between the ends of the tubes (17a, 17b) has a length comprised between 1 and 2 cm.

19. An apparatus according to claim 12, characterized in that said carrier gas source (13) is suitable for providing ambient air.

20. An apparatus according to claim 12, characterized in that the tubes (17) connecting its various components are made of a material chosen between PTFE and stainless steel.

* * * * *